United States Patent
Fischer

(10) Patent No.: US 7,002,678 B1
(45) Date of Patent: Feb. 21, 2006

(54) AVOIDANCE OF POISONING DURING ANESTHESIA

(75) Inventor: Bernhard Fischer, Leonberg (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 10/069,892

(22) PCT Filed: Aug. 28, 1999

(86) PCT No.: PCT/EP99/06348

§ 371 (c)(1),
(2), (4) Date: Feb. 27, 2002

(87) PCT Pub. No.: WO01/15762

PCT Pub. Date: Mar. 8, 2001

(51) Int. Cl.
*G01J 3/44* (2006.01)

(52) U.S. Cl. ..................................................... 356/301

(58) Field of Classification Search ................ 356/301, 356/339, 343

See application file for complete search history.

(56) References Cited

U.S. PATENT DOCUMENTS

| | | | | |
|---|---|---|---|---|
| 4,784,486 A | * | 11/1988 | Van Wagenen et al. | 356/301 |
| 5,450,193 A | * | 9/1995 | Carlsen et al. | 356/301 |
| 5,929,981 A | * | 7/1999 | Keilbach | 356/73 |
| 6,072,577 A | * | 6/2000 | Wunderling et al. | 356/301 |
| 6,228,150 B1 | * | 5/2001 | Armstrong et al. | 95/139 |

OTHER PUBLICATIONS

Kronen, "Anesthetic Management Of the Horse . . . ," Jan. 2003, International Veterinary Information Service.*

* cited by examiner

Primary Examiner—Layla G. Lauchman
(74) Attorney, Agent, or Firm—Thomas M. Lundin

(57) ABSTRACT

For avoiding poisoning effects during anesthesia, the quantitative amount of an anesthetic agent degradation product, preferably carbon monoxide CO and/or trifluoromethane $CHF_3$, in an anesthetic gas mixture is determined. When the determined quantitative amount of the anesthetic agent degradation product in the anesthetic gas mixture exceeds a given threshold, an alarm is provided. This is preferably accomplished by measuring a Raman spectrum of the gas mixture, and determining the quantitative amount of the anesthetic agent degradation product in the gas mixture by comparing the measured Raman spectrum with a reference spectrum of the anesthetic agent degradation product.

6 Claims, 1 Drawing Sheet

AVOIDANCE OF POISONING DURING ANESTHESIA

BACKGROUND OF THE INVENTION

The present invention relates to poisoning effects during anesthesia.

During anesthesia with one of the agents desflurane, isoflurane or enflurane, it has been observed that patients can accidentally become exposed to carbon monoxide, CO, thus leading to an inadvertent CO-poisoning of the patient. Peter B. Berry et al. in "*Severe Carbon Monoxide Poisoning during Desflurane Anesthesia*", Anesthesiology V 90, No. 2, February 1999, p. 613 report 36% COHb as highest CO level in blood due to this effect, i.e. 36% of hemoglobin loaded with CO (instead of oxygen) after only 15 min of anesthesia time with desflurane. A degradation of the anesthetic agent used in conjunction with Baralime or Sodalime, generally used as absorber material for $CO_2$ in circle breathing systems, has been identified as origin of this exposure. It has been found that degradation of the agent occurs under a condition that the $CO_2$ absorber material is too dry. Carbon monoxide, CO, has been identified as one of the degradation products.

Usually, the accidental CO exposure goes undetected, because CO is not identified or measured by the commercially available medical gas monitors. Although clinicians are aware of the potential problem, its early recognition and immediate remedy requires experience and a thorough knowledge of the behavior of the monitoring equipment used. In the above case, described by Peter B. Berry et al., the detection occurred through a sequence of strange observations, $1^{st}$ the oxygen saturation of the patient decreased to 93% in spite of a fresh gas flow with 100% oxygen, $2^{nd}$ the gas analyzer being set to automatic agent identification mode suddenly switched to "enflurane" in spite of the desflurane used. Only then, the clinicians suspected CO poisoning resulting from desiccation of the $CO_2$ absorber. A blood analysis for COHb confirmed that suspicion.

The intoxication by CO occurs through the strong binding of this molecule to hemoglobin in competition to the binding of oxygen. The affinity of hemoglobin to CO, however, is 300 times stronger than to oxygen. Therefore, it is a question of the dosage of CO that determines the COHb level in blood. Harrison N. et al. in Anesthesia, Vol. 51, p 1037–1040 (1996) notes that a CO level of 0.1% for 1 h gives a COHb level of approximately 30% and evidence of moderate to severe toxicity. In the case reported by Peter B. Berry et al., the measured COHb level was 36% after 15 min of anesthesia time. It can be concluded that the CO concentration in the inhaled gas stream in his reported case must have been of the order of 0.5%.

Gas analyzers normally applied in anesthetic environments are based on gas detection by absorption measurements. Primarily, the infrared (IR) spectral region is used. The unusual behavior of the gas analyzer in the above reported case was explained by the similarity of the infrared absorption spectrum between another degradation product trifluoromethane, $CHF_3$, and enflurane, thus leading to the erroneous identification of the anesthetic agent.

It has been speculated by Harvey J. Woehlck in "*Severe Intraoperative CO Poisoning*", Anesthesiology V 90, No. 2, February 1999, p. 353 (Editorial), that a very large number of patients are at risk to be exposed to undetected CO levels, in particular the first cases in the morning or cases on anesthesia machines that are infrequently used. Also, the use of a high flow of fresh (dry) gas enhances the likelihood that the $CO_2$ absorber material becomes desiccated and starts to break down the agent molecules.

The complete avoidance of the described problem would require strict discipline with the renewal/exchange routine of the $CO_2$ absorber material (cf. Harvey J. Woehick et al., Reduction in the Incidence of Carbon Monoxide Exposures in Humans Undergoing General Anesthesia, Anesthesiology V87, No 2, August 1997, p. 228). However, since this strict discipline with the renewal/exchange routine appears to be hardly feasible, an early and unambiguous identification of CO gas would be desirable. The gas monitors presently used in clinics, however, are not capable of detecting CO and react only indefinitely to its presence in the breathing gas mixture and mostly provide erroneous information to the user.

SUMMARY OF THE INVENTION

It is therefore an object of the invention to avoid poisoning effects during anesthesia. The object is solved by the independent claims. Preferred embodiments are shown by the dependent claims.

According to the invention, the CO concentration in a respiration gas is directly and/or indirectly measured in a substantially continuous monitoring process. An alarm will be provided when the monitored concentration exceeds one or more given threshold values. Thus, a timely warning can be issued so that the clinical personnel can replace the $CO_2$ absorber material before any harm will be done to the patient.

An indirect monitoring of the CO concentration in a respiration gas is applied by measuring a by-product of the anesthetic agent degradation process other than CO. Preferably, a by-product is selected which is absorbed in the body to a much lower degree than CO and thus easier to detect than CO. The by-product is thus employed as an indicator for the presence of CO. Preferably, trifluoromethane, $CHF_3$, is employed as such an indicator. $CHF_3$ can be detected using Raman or IR spectroscopy.

It has been shown that the physiologically relatively harmless $CHF_3$ provides an excellent indicator for the presence of the dangerous CO. Since CO is virtually "sucked" by the lungs into the blood, the CO concentration in the respiration circle normally remains relatively low. The concentration of $CHF_3$, in contrast thereto, will be accumulated in the respiration circle, because $CHF_3$ is normally bound or absorbed in the body to a much lower degree than CO. Therefore, the concentration of CHF, in the respiration circle will be normally much higher than the concentration of CO and is thus much easier to detect.

A direct monitoring of the CO concentration in a respiration gas is applied using Raman spectroscopy for directly detecting the presence of anesthetic agent degradation products in a respiration gas such as CO and/or any other degradation product, like $CHF_3$, which can be employed as an indicator for the presence of CO.

The invention preferably applies Raman scattering for gas analyzing purposes. Gas detection, in general, is accomplished either by using optical absorption or by scattering of light. Scattering of light occurs as a consequence of the electronic polarizability of the electron cloud around atoms and molecules. Most incident photons are scattered by the sample with no change in frequency in a process known as Rayleigh scattering. Rayleigh scattering occurs from molecular as well as atomic species. However, with a small probability the scattered photons have frequencies $f_0+/-f_1$, where $f_0$ is the frequency of the incident photon and $f_1$ is the frequency of a molecular vibration. This process is called Raman scattering. The modification of the scattered photons results from the incident photons either gaining energy from or losing energy to the vibrational or rotational motion of the molecule. Since complex molecules exist in a number of different rotational and vibrational states (depending on the temperature), many different values of $f_1$ are possible. Consequently, the Raman spectrum of a Raman-active gas will consist of a large number of scattered lines. Simple diatomic molecules like oxygen, $O_2$, or nitrogen, $N_2$, have just one Raman line.

To enhance the observation of the radiation at $f_0+/-f_1$, the scattered radiation is observed perpendicularly to the incident beam. To provide high intensity incident radiation and to enable the observation of lines where $f_1$ is small (due to rotational changes), the source of a Raman spectrometer is normally chosen as a monochromatic visible laser. The scattered radiation can then be analyzed by use of a scanning optical monochromator with a photomultiplier tube or another suitable photo detector.

Gas analyzers employing Raman spectroscopy can be calibrated to various Raman-active gases. The spectral "fingerprint" of Raman-active gases can be used to identify constituents of even very complex gas mixtures, and the relative intensity of the spectral contributions by each member gas is used to quantify the gases.

In a preferred embodiment of the invention, a gas analyzer employing Raman spectroscopy is calibrated to one or more anesthetic agent degradation products such as $CHF_3$, CO and/or other species of interest, normally in addition to the usual respiratory and anesthetic gases. Calibration herein means that a reference spectrum of the respective Raman-active gas is stored and will be used for detecting the respective Raman-active gas. As soon as the Raman gas monitor detects amounts of unwanted species exceeding pre-given threshold values, a warning sign will be generated thus alerting e.g. the clinician and giving direct and clear information about the origin and nature of the problem.

In one embodiment, a (direct) CO detection and monitoring is applied for generating a warning signal against impending CO poisoning. In another embodiment, the detection of any other degradation product like the $CHF_3$ compound is employed. $CHF_3$ gives a very strong Raman signal, and it has been verified that the lower detection limit is well below 0.1%. CO is strongly bound to hemoglobin (the affinity of Hb to CO is 300 times larger than to oxygen) such that inhaled gas gets depleted from CO very effectively, while the $CHF_3$ stays in the breathing circuit and rapidly enriches to higher concentrations. Therefore, $CHF_3$ represents a fairly good indicator gas for CO presence.

In a preferred embodiment of the invention, a Raman gas analyzer is employed using a laser source in the visible spectral region to excite the Raman spectrum. The Raman gas analyzer might further be equipped with a spectrometer to measure Raman lines in a spectral range of preferably about 200 nm from the excitation wavelength. This gas analyzer can be calibrated for Raman-active gases by exposing the Raman measurement cell to a pure sample (or diluted mixture) containing this gas and recording the respective Raman spectrum as a calibration spectrum. This way, the analyzer can be calibrated for CO and/or $CHF_3$, also in addition to the other respiratory and anesthetic gases of interest to the user.

An alarming algorithm is implemented preferably triggered by the detection of CO and/or $CHF_3$ in the breathing gas stream during clinical use. This alarm indicates to a user to check the $CO_2$ absorber and to exchange it against fresh material immediately in order to avoid CO poisoning of the patient.

The gas monitor in accordance with the present invention provides an early warning capability against CO poisoning and permits that accidental CO poisoning by the described degradation process can be reliably avoided. Although there is great uncertainty in the medical literature about the true morbidity from interoperative CO poisoning and about the resulting economic damage, it is well known that even moderate levels of a few percentage of COHb in patients undergoing cardiac, cranial, or spinal surgery may cause severe oxygen deficiencies. Prolonged oxygen deficiency leads to neurological disorders.

A further possibility for determining anesthetic agent degradation products is to use infrared absorption spectroscopy for the detection of CO and/or $CHF_3$. However, the larger widths and overlaps in IR absorption bands of the species of interest render the identification task to be fairly complex. A currently available medical gas analyzer would have to be fitted with additional optical filters, and the algorithms would have to be changed accordingly. The effort for both is very costly.

BRIEF DESCRIPTION OF THE DRAWINGS

Other objects and many of the attendant advantages of the present invention will be readily appreciated and become better understood by reference to the following detailed description when considering in connection with the accompanied drawings. Features that are substantially or functionally equal or similar will be referred to with the same reference sign(s).

DETAILED DESCRIPTION OF THE INVENTION

Figure 1:
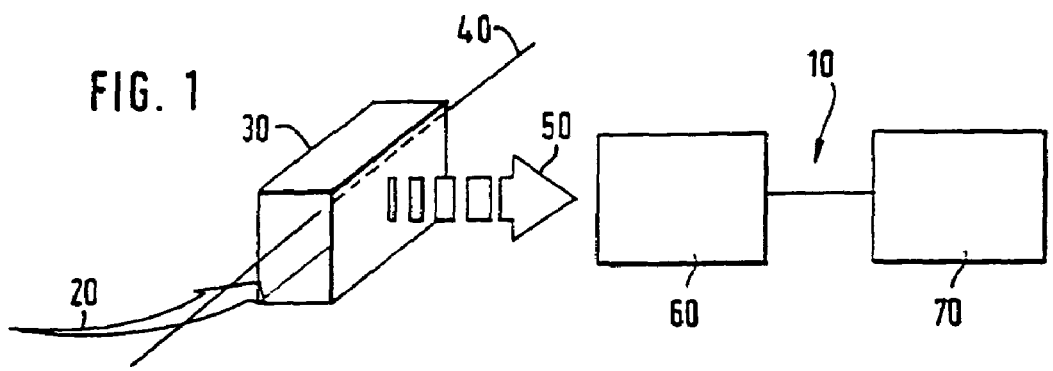
FIG. 1 depicts the schematic view of a gas monitor 10 according to the invention.

FIG. 1 depicts the schematic view of a gas monitor 10 according to the invention. A gas flow 20 with a gas mixture such as a respiration gas is directed through a sample cell 30. An incident light beam 40, e.g. from a laser source, is scattered in the sample cell 30 and a scattering light 50 is received by a spectrograph 60. The spectrograph 60 is further coupled to a processing unit 70 for determining the composition of the gas mixture in the gas flow 20.

The processing unit 70 is preferably further connected (not shown) to the source of the light beam 40 for receiving information about the light beam 40, such as the intensity. The processing unit 70 is preferably further coupled to a (not shown) pressure determining means and a temperature sensor within the sample cell 30 for receiving information about the pressure and temperature therein.

In a first step, the spectrograph 60 of the gas monitor 10 measures the Raman spectrum of the gas mixture. In a second step, the processing unit 70 then determines the quantitative amount of one or more anesthetic agent degradation products in the gas mixture of the gas flow 20 by comparing the measured Raman spectrum with stored reference spectra of anesthetic agent degradation products. Each reference spectrum generally represents the Raman spectrum for the pure gas component, determined under known conditions, e.g. a known condition of pressure and/or temperature within the sample cell 30 and of the intensity of the incident light beam 40. Accordingly, reference spectra can be applied already representing a defined gas mixture. The proportion of the measured spectrum to each reference spectrum provides a direct measure of the proportion of the individual gas component (represented by the reference spectrum) in the gas mixture.

The assignment of the peak(s) in the measured spectrum to the individual gas component(s) can be done as known in the art, e.g. by comparing the wavelength(s) of the peak(s) with the wavelength(s) of the reference spectrum/spectra of the individual gas component(s).

The comparison of the measured Raman spectra with the reference Raman spectra is preferably accomplished by determining the ratio of the amplitudes (intensities) for each wavelength channel of the spectrograph. However, other comparison methods e.g. by means of the peak area or the like can be applied accordingly.

In case that a certain individual gas component reveals more than one Raman line, all lines are preferably attenuated substantially evenly, so that, for the purpose of the invention, it is normally sufficient to evaluate only one Raman line for each gas component for determining the proportion of the individual gas component in the gas mixture.

The reference spectra comprising the wavelength positions and intensities are preferably determined by previous measurements and can be stored e.g. in a calibration matrix.

In case that the actual measuring conditions deviate from the measuring conditions of the reference spectra, the measured spectra have to be corrected, e.g. for the effects of pressure, temperature, and light intensity changes, using well-known algorithms.

Figure 2:
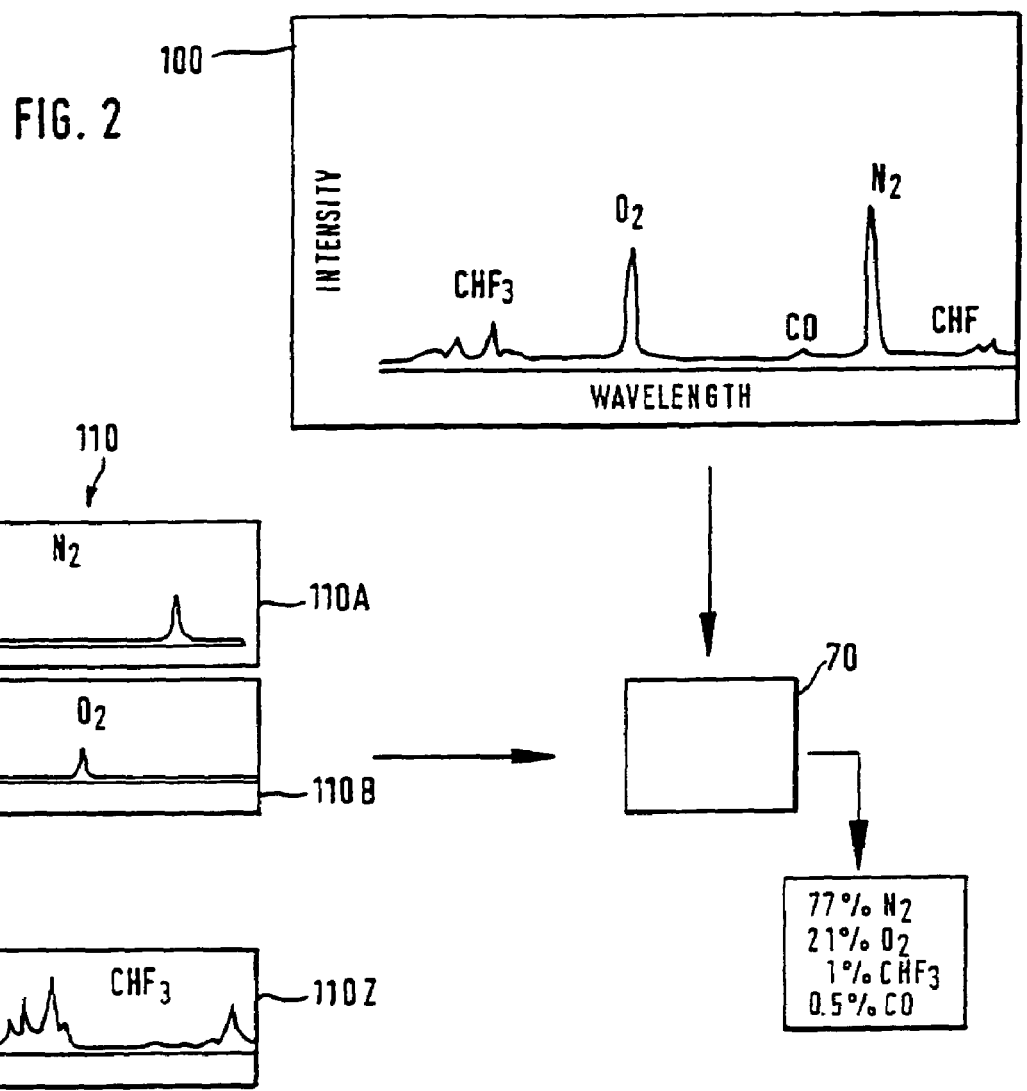
FIG. 2 shows an example of a measurement of a composition of a gas mixture with a number of gas constituents.

FIG. 2 shows an example of a measurement of a composition of a gas mixture with a number of gas constituents. The spectrograph 60 measures a Raman spectrum 100 of the gas mixture. The wavelength position and intensities of a plurality of Raman lines are stored in a calibration matrix 110 with a plurality of individual reference spectra 110A . . . 110Z for several gas constituents.

The measured spectrum 100 of the gas mixture is compared with the respective reference spectra 110A, 110B of the calibration matrix 110. The proportions of the peak levels from the reference spectra 110A, 110B, and 110Z to the measured spectrum 100 provides a direct measure for the proportions of the individual components in the gas mixture. In the example of FIG. 2, the wavelength and characteristics of the measured peaks refer to $N_2$, $O_2$, $CHF_3$, and CO. In this example, the peak $N_2$ shall represents 77% of the reference peak for $N_2$ in the reference spectrum 110A, the peak $O_2$ represents 21% of the reference peak for $O_2$ in the reference spectrum 110B, and both $CHF_3$ peaks (to the very left and right in the spectrum 100) represents 1% of the reference peak for $CHF_3$ in the reference spectrum 110Z. The peak CO represents about 0.5% of the reference peak for CO (not shown in 110). Accordingly, the gas composition of the measured spectrum 100 is: 77% of $N_2$, 21% of $O_2$, 1% of $CHF_3$, and about 0.5% of CO.

When the determined quantitative amount of one or more of the anesthetic agent degradation products in the gas mixture exceeds given threshold values for each of the degradation products, an alarm will given in a third step. The determination of reasonable threshold values for the detection of the degradation products is of course dependent on the sensitivity of the specific embodiment of the measurement system. Since one dangerous aspect of CO poisoning is the dose (the dose being the concentration multiplied by the exposure time) deposited in the blood hemoglobin, the optimization of the threshold values should preferably take into account both the detection limits for the degradation products as well as the system's integration time associated with those detection limits. On one hand, it is desirable to have threshold values as low as possible in order to generate a warning as early as possible, but, on the other hand, false-positive alarms triggered in an overly sensitive system are to be avoided, too. In a preferred embodiment, threshold values of 0.5% for $CHF_3$ and/or 0.2% for CO have been proved satisfactory. If more than one degradation product are monitored simultaneously a further increase in reliability of the alarm can be obtained from correlating the detection of these products at concentrations above the set threshold values.

In another preferred embodiment, only one of the anesthetic agent degradation products is used for monitoring possible CO-poisoning of patients in anesthesia. Preferably, only $CHF_3$ will be monitored since $CHF_3$ provides a sufficiently strong Raman signal and it has been verified that the lower detection limit is well below 0.1%.

What is claimed is:

1. A system (10) for avoiding poisoning effects during anesthesia, comprising:
   determining means (60, 70) for determining the quantitative amount of an anesthetic agent degradation product in an anesthetic gas mixture, and
   alarm means for providing an alarm when the determined quantitative amount of the anesthetic agent degradation product in the anesthetic gas mixture exceeds a given threshold,
   wherein the anesthetic agent degradation product is trifluoromethane, $CHF_3$, as an indicator for the presence of CO in the gas mixture.

2. The system of claim 1, wherein the determining means (60, 70) comprises:
   measuring means (60) for measuring a Raman spectrum of the gas mixture, and
   a processing unit (70) for determining the quantitative amount of the anesthetic agent degradation product in the gas mixture by comparing the measured Raman spectrum with a reference spectrum of the anesthetic agent degradation product.

3. A system (10) for avoiding CO poisoning effects during anesthetic caused by anesthetic agent degradation products in a gas mixture such as a respiration gas, comprising:
   means (60) for measuring a Raman spectrum of the gas mixture,
   a processing unit (70) for determining the quantitative amount of at least one of the anesthetic agent degradation products in the gas mixture by comparing the measured Raman spectrum with a reference spectrum of the at least one anesthetic agent degradation products, and
   means for providing an alarm when the determined quantitative amount of the anesthetic agent degradation product in the gas mixture exceeds a given threshold, wherein the anesthetic agent degradation product is trifluoromethane, $CHF_3$, as an indicator for the presence of CO in the gas mixture.

4. A method for avoiding poisoning effects during anesthesia, comprising the steps of:
   (a) determining the quantitative amount of an anesthetic agent degradation product in an anesthetic gas mixture, and
   (b) providing an alarm when the determined quantitative amount of the anesthetic agent degradation product in the anesthetic gas mixture exceeds a given threshold wherein the anesthetic agent degradation product is trifluoromethane, $CHF_3$, as in an indicator for the presence of CO in the gas mixture.

5. The method of claim 4, wherein the step (b) comprises the steps of:
(c) measuring a Raman spectrum of the gas mixture, and
(d) determining the quantitative amount of the anesthetic agent degradation product in the gas mixture by comparing the measured Raman spectrum with a reference spectrum of the anesthetic agent degradation product.

6. Use of a Raman spectrometer (60, 70) for determining the quantitative amount of an anesthetic agent degradation product in a gas mixture wherein the anesthetic agent degradation product is trifluoromethane, $CHF_3$, as an indicator for the presence of CO in the gas mixture.

* * * * *